(12) United States Patent
Byström et al.

(10) Patent No.: US 11,192,076 B2
(45) Date of Patent: Dec. 7, 2021

(54) FLOW-PROMOTING DEVICE, A REACTOR ARRANGEMENT AND THE USE OF SUCH FLOW-PROMOTING DEVICE

(71) Applicant: SPINCHEM AB, Umeå (SE)

(72) Inventors: Emil Byström, Tavelsjo (SE); Knut Irgum, Bullmark (SE); Erik Löfgren, Umeå (SE); Christopher Öberg, Umeå (SE)

(73) Assignee: SPINCHEM AB, Umea (SE)

( * ) Notice: Subject to any disclaimer, the term of this patent is extended or adjusted under 35 U.S.C. 154(b) by 186 days.

(21) Appl. No.: 16/491,235

(22) PCT Filed: Feb. 9, 2018

(86) PCT No.: PCT/EP2018/053320
§ 371 (c)(1),
(2) Date: Sep. 5, 2019

(87) PCT Pub. No.: WO2018/162174
PCT Pub. Date: Sep. 13, 2018

(65) Prior Publication Data
US 2020/0009519 A1    Jan. 9, 2020

(30) Foreign Application Priority Data

Mar. 6, 2017  (SE) .................................. 1750248-5

(51) Int. Cl.
*B01J 8/10*  (2006.01)
*B01J 19/18*  (2006.01)
(Continued)

(52) U.S. Cl.
CPC ............. *B01F 13/0818* (2013.01); *B01J 8/10* (2013.01); *B01J 8/42* (2013.01); *B01J 19/0066* (2013.01);
(Continued)

(58) Field of Classification Search
None
See application file for complete search history.

(56) References Cited

U.S. PATENT DOCUMENTS 8,808,636 B2 *  8/2014  Persson ................... B01F 7/006
                                                                422/209
2004/0252582 A1 * 12/2004  Bucher ............... B01F 13/0863
                                                                366/273
(Continued)

FOREIGN PATENT DOCUMENTS

GB          2475401 A  *  5/2011  .......... B01F 13/0055
JP       H-0655131 B      7/1994
(Continued)

OTHER PUBLICATIONS

International Search Report for Application No. PCT/EP2018/053320, dated Apr. 24, 2018.

*Primary Examiner* — Jennifer A Leung
(74) *Attorney, Agent, or Firm* — Moser Taboada

(57) ABSTRACT

The invention refers to a flow-promoting device (100; 100'; 100") for performing a biological or chemical transformation, or physical or chemical trapping from, or release of agents to, a fluidic medium. The flow-promoting device (100; 100'; 100") comprises a ferromagnetic material (5) and a retaining structure (1; 1'; 1"), the retaining structure having a compartment (9; 9") defined by a permeable material (11; 11"). The retaining structure (1; 1'; 1") comprises a top wall (3; 3") and a circumferential side wall (4; 4"), wherein the top wall (3; 3") and the circumferential side wall (4; 4") is formed mainly by said permeable material (11; 11"). The compartment (9; 9") of the retaining structure (1; 1'; 1") is arranged to contain at least one fluid-permeable solid reaction member.

12 Claims, 5 Drawing Sheets

Figure 1:
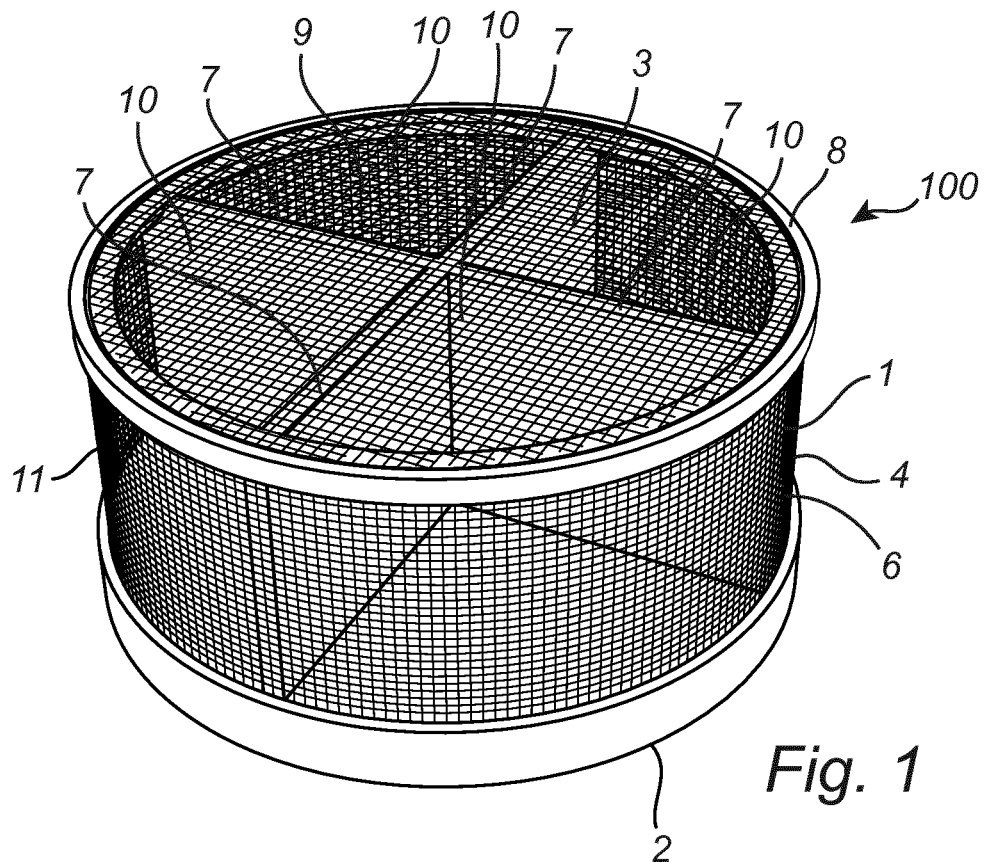

(51) Int. Cl.
  *B01F 13/08* (2006.01)
  *B01J 8/42* (2006.01)
  *B01J 19/28* (2006.01)
  *B01J 19/00* (2006.01)

(52) U.S. Cl.
  CPC ............... *B01J 19/18* (2013.01); *B01J 19/28* (2013.01); *B01J 2208/00814* (2013.01); *B01J 2208/00876* (2013.01); *B01J 2208/00884* (2013.01); *B01J 2208/00938* (2013.01)

(56) References Cited

U.S. PATENT DOCUMENTS

| | | | |
|---|---|---|---|
| 2011/0003375 A1* | 1/2011 | Ashe | B01F 13/1013 435/303.3 |
| 2012/0156111 A1 | 6/2012 | Ramos et al. | |
| 2014/0322093 A1 | 10/2014 | Persson et al. | |

FOREIGN PATENT DOCUMENTS

| | | | |
|---|---|---|---|
| SE | 539074 C2 | 4/2017 | |
| WO | WO-9730784 A1 * | 8/1997 | ............. C07K 1/045 |
| WO | WO-2010/139337 A1 | 12/2010 | |
| WO | WO 2011/098570 A2 | 8/2011 | |
| WO | WO 2016186941 A1 | 11/2016 | |

* cited by examiner

FLOW-PROMOTING DEVICE, A REACTOR ARRANGEMENT AND THE USE OF SUCH FLOW-PROMOTING DEVICE

FIELD OF INVENTION

The present invention refers to a flow-promoting device, a reactor arrangement comprising such flow-promoting device and the use of such flow-promoting device.

BACKGROUND OF THE INVENTION

Heterogeneous processes in chemistry and biotechnology are unit operations that encompass a solid member contacting a fluidic medium carrying reactants or other agents, sample solutes, and/or products of the interactive processing of fluid-conveyed agent(s) with the solid members. The solid members may by way of example be immobilized chemical reagents, catalysts, scavengers, reaction supports, trapping sorbents, or immobilized biological materials such as enzymes, or cells or fragments thereof.

One way of performing these kind of heterogeneous processes is by using flow-promoting devices or rotating flow cells containing at least one solid member.

WO 2010/139337 discloses a submerged perfusion bioreactor to be used for cell culturing, enzymatic reactions or filtering of fluid. The device comprises a body having a central aperture in which a rotating means is received. The top and/or the bottom wall of the device comprise a central inlet orifice. The rim interconnecting the top and bottom wall comprises at least one recessed portion forming a cavity for cell culturing. The culturing is e.g. made on scaffolds inserted into the cavities. As the rotating means is set to rotate inside the aperture, the fluid is pumped into the aperture via the central inlet orifice and pumped in the radial direction through the at least one outlet channel.

JP 2005046822 discloses another example in form of a distributing fluid rotor to be used in operations such as filtration, adsorption, separation and reaction of materials contained in the fluid, or concentration and extraction by another fluid, or a solid-fluid or a fluid reciprocal reaction. The distributing fluid rotor is disclosed as a body in the form of a puck or a bar and has a central inlet. The central inlet communicates with one or several pipe shaped flow channels extending in the radial direction towards an outlet formed in a circumferential side wall. The flow channels are provided with a cartridge or a filter. As the fluid rotor is set to rotate, a vortex is formed sucking the fluid into the flow channels via the central inlet. The fluid is released via the outlets of the flow channels.

Prior art rely on the creation of a vortex which aspirates the fluidic medium into the interior of the body via a central opening and then out of the body via radial channels. Although creation of a vortex is an effective way of directing a fluid flow into a compartment, it has been noted that the vortex formation may in some cases cause problems when it comes to porous solid reaction members or loosely stacked solid reaction members contained in the body. The vortex formation may cause an unwanted effect in the form of entrapment of gas in the porous structure and an accompanying gas lock. Further, the radial channels provide a limited contact area between the solid reaction members and the fluidic medium. This affects the process tie and also restricts the overall efficiency.

SUMMARY OF THE INVENTION

It is an object of the present invention to provide a flow-promoting device that allows shortened process time with at least a remained efficiency and which also reduces the risk of gas being entrapped or locked. Further, the flow-promoting device should allow for an easy operation together with vessels of different types and contents without undue manual contact and handling of the flow-promoting device.

According to a first aspect, the invention provides a flow-promoting device for performing a biological or chemical transformation, or physical or chemical trapping from, or release of agents to, a fluidic medium, said flow-promoting device comprising a ferromagnetic material and a retaining structure, the retaining structure having a compartment defined by a permeable material, wherein the retaining structure comprises a top wall and a circumferential side wall, wherein the top wall and the circumferential side wall is formed mainly by said permeable material, and the compartment of the retaining structure is arranged to contain at least one fluid-permeable solid reaction member, whereby when the flow-promoting device is submerged into a fluidic medium and the flow-promoting device is subjected to an alternating magnetic field, the flow-promoting device is set to rotate, thereby causing a flow of fluidic medium into and through the compartment via said permeable material.

When the flow-promoting device is sub-merged into a vessel containing a fluidic medium and subjected to an alternating magnetic field of an external magnetic or electromagnetic actuator, the flow-promoting device will propel in a rotational manner inside the vessel. During the rotation, the fluidic medium will be caused to aspirated via at least the top wall which is mainly made of the permeable material, into the retaining structure and hence come in contact with the at least one fluid-permeable solid reaction member arranged in the compartment before being discharged via the permeable circumferential side walls. The at least one fluid-permeable solid reaction member will accordingly be percolated by said fluidic medium, allowing at least one agent distributed in the fluidic flow to undergo a chemical process such as a biological or chemical transformation, or a physical or chemical trapping from, or release of agents to the fluidic medium. Since the top wall is mainly made of permeable material, the fluidic medium will be allowed to be aspirated across essentially the full area of the top wall, whereby no vortex is formed that may cause entrapment of gas or form gas locking in/around the fluid-permeable solid reaction members.

Further, by the walls of the retaining structure being formed mainly by a permeable material and whereby the fluidic medium is allowed to aspirated into the compartment of the retaining structure across the full top surface, the available contact surface between the fluidic medium and the fluid-permeable solid reaction members may be substantially increased as compared to prior art devices which use a central inlet and radially extending outlet channels. This allows a reduced process time.

The top wall may have a continuous extension across its full surface extension and not comprise any central inlet opening via which the compartment communicates with the ambience. The top surface as such must not be flat but may have other extensions such as a dome shape.

The permeable material may be a mesh material, said mesh material having an inherent stiffness thereby forming a self-supporting retaining structure, or said mesh material may be supported by a frame expanding said compartment. The mesh material should have a density that retains the fluid-permeable solid reaction members inside the compartment. This is especially the case if the solid reaction members should be loosely packed particles.

The retaining structure may comprise at least one partition wall dividing the compartment into at least two chambers. Each chamber may be arranged to contain at least one fluid-permeable solid reaction member. The fluid-permeable solid reaction members may be loosely received in the chambers.

The compartment or the at least two chambers of the flow-promoting device may be arranged to receive at least one cartridge adapted to contain the at least one fluid-permeable solid reaction member. The fluid-permeable solid reaction member may be loosely received in the cartridge.

The ferromagnetic material may be a unitary body fixedly arranged to the retaining structure. This may be made by the unitary body being in-molded in the retaining structure, fixed thereto by using an adhesive or being received in a compartment in the retaining structure.

The retaining structure may be a body comprised of one or more fluid permeable self-supporting material(s) of spatially homogenous or composite design, exemplified but not limited to, porous monoliths made from organic or inorganic precursors, open cell foams or sponges, porous (hydro)gels, cryogels, or a combination thereof, in which body said fluid-permeable solid reaction members are incorporated. Accordingly, the outer boundaries provided by such fluid permeable self-supporting material(s) will form a top wall and a circumferential side wall of the retaining structure. Such retaining structure may by way of example have a puck-shape.

The ferromagnetic material may be particulate, and be integrated and distributed in the body formed by said one or more fluid-permeable self-supporting material(s). The integration and distribution may be homogenous or restricted to well-defined areas such as a layer integrated in the body.

The ferromagnetic material may be a longitudinal body fixedly arranged to the flow-promoting device and extending in a geometrical plane extending through a centre of the flow-promoting device and in parallel with the rotational axis of the flow-promoting device. The longitudinal ferromagnetic body may be a bar magnet. The longitudinal ferromagnetic body may be integrated in a partition wall coinciding with the geometrical plane and which thereby divides the compartment of the retaining structure in two separate chambers.

According to another aspect, the invention refers to a reactor arrangement, the arrangement comprising a flow-promoting device according to any of the features given above, and a supporting structure, wherein the supporting structure is arranged to removably receive the flow-promoting device, and allow the flow-promoting device to rotate inside the supporting structure when subjected to an alternating magnetic field of an external magnetic or electromagnetic actuator. The supporting structure may ensure a proper orientation of the flow-promoting device inside a vessel.

The supporting structure may comprise an abutment portion against which the flow-promoting device is arranged to abut during rotation. The abutment portion may be provided as a flat surface and if necessary with a guidance, centralizing the flow-promoting device in view of its rotational axis and thereby preventing wobbling. The abutment portion may be provided with low friction characteristics. The low friction may be provided by the surface texture or by a low friction coating.

The supporting structure may further comprise a restriction portion opposite the abutment portion, wherein the flow-promoting device is arranged to be removably received between said restriction portion and said abutment portion.

The flow-promoting device will be retained inside the supporting structure as seen in a direction perpendicular to the abutment portion. Thereby the flow-promoting device is prevented from falling out of the supporting structure in the event the same should be designed to be turned upside down during handling. The latter may be the case if the supporting structure also is arranged to form part of a closure. Also, the overall handling of the flow-promoting device in combination with a vessel filled with a fluidic medium will be facilitated since the position of the flow-promoting device more or less will be immediately correct when subjected to the fluidic medium. This is especially the case if the vessel has the shape of a tube with a diameter marginally larger than the outer dimensions of the flow-promoting device. The restriction portion will also provide the additional effect that it will prevent any formation of a vortex as the flow-promoting device is set to rotate. The supporting structure may be arranged to removably receive the flow-promoting device in a direction in parallel to the abutment portion. Also, removal of the flow-promoting device after use may be facilitated. The flow-promoting device may be handled as one unitary piece together with the supporting structure which unitary piece easily can be moved from one vessel to another. This may e.g. be the case if the flow-promoting device is used to capture a substance in one vessel and then moved to another vessel and fluid where such captured substance is to be eluted.

The reactor arrangement may further comprise a closure arranged to be mounted to a vessel, and wherein the supporting structure is removable arranged to the closure, fixed to the closure or integrally formed with the closure. The flow-promoting device may be inserted by the operator manually into the supporting structure and hence into the closure upon use, or be provided as a pre-assembled off-the-shelf arrangement. The vessel to be used may be filled up with the intended fluidic medium and then closed by mounting the closure. The thus closed vessel may now be turned upside down and positioned on a stirring plate in the form of an external magnetic or electromagnetic actuator while resting on the closure. When activating the actuator, the flow-promoting device will rotate inside the vessel in a controlled manner. Once the reaction has reached the target level, the closure may be removed together with the flow-promoting device whereby free access to the fluidic medium is provided for without any contact with the fluidic medium and/or the flow-promoting device. Depending on intended use, the closure still containing the flow-promoting device may be moved to another vessel for continued processing together with a different fluidic medium. Accordingly, improved working conditions are provided for.

According to yet another aspect, the invention refers to the use of a flow-promoting device with the features given above for performing a biological or chemical transformation, or physical or chemical trapping from, or release of agents to, a fluidic medium. The flow-promoting device may be used either as a stand-alone device or together with a supporting structure. The use may take place in a separate vessel such as a test tube or a flask of any type. Also the vessel may be arranged in a tray to be arranged on an external magnetic or electromagnetic actuator, the tray as such comprising several vessels. Each such separate vessel may be provided with a flow-promoting device. It is to be understood that the vessel, no matter type, may be provided with at least one baffle to prevent vortex formation.

BRIEF DESCRIPTION OF THE ENCLOSED FIGURES

The present invention will be further disclosed with reference to the enclosed figures, in which:

FIG. 1 discloses a perspective top view of a first embodiment of a flow-promoting device.

Figure 2:
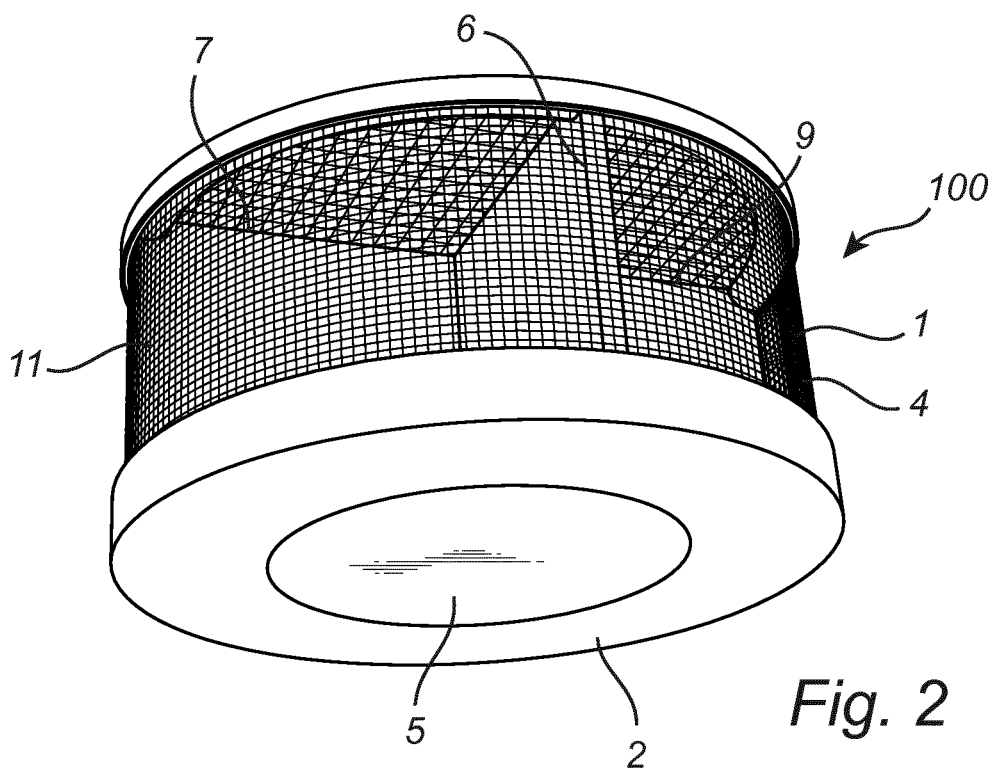

FIG. 2 discloses a perspective bottom view of a first embodiment of a flow-promoting device.

Figure 3A:
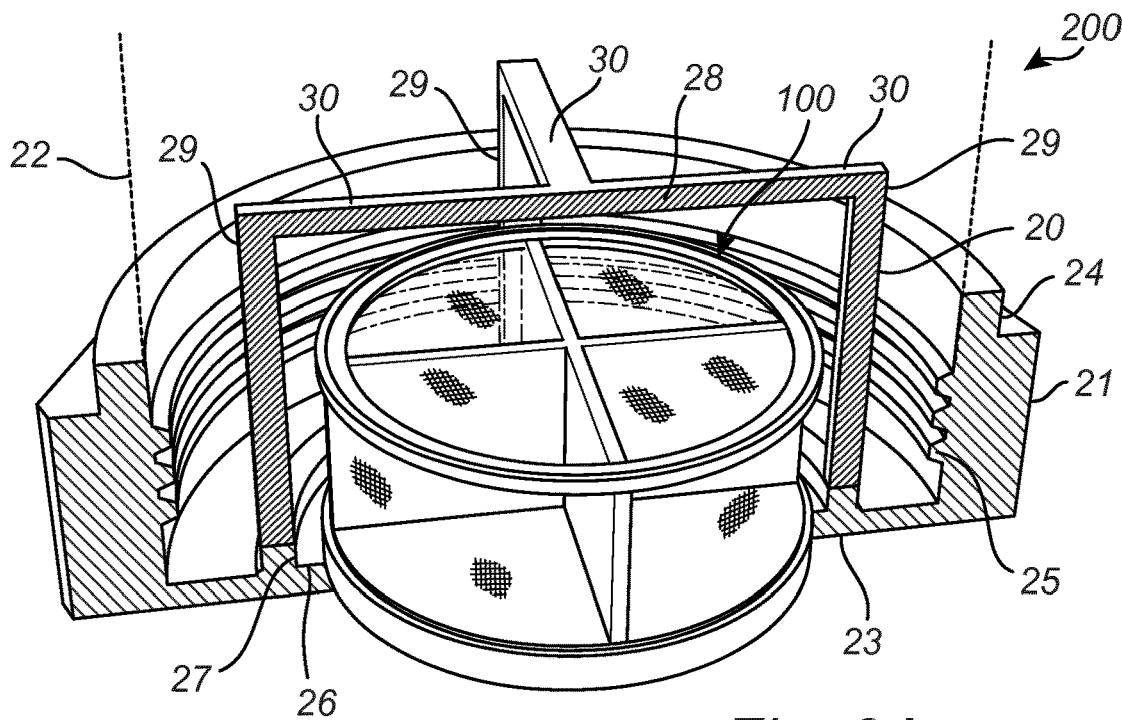
Figure 3B:
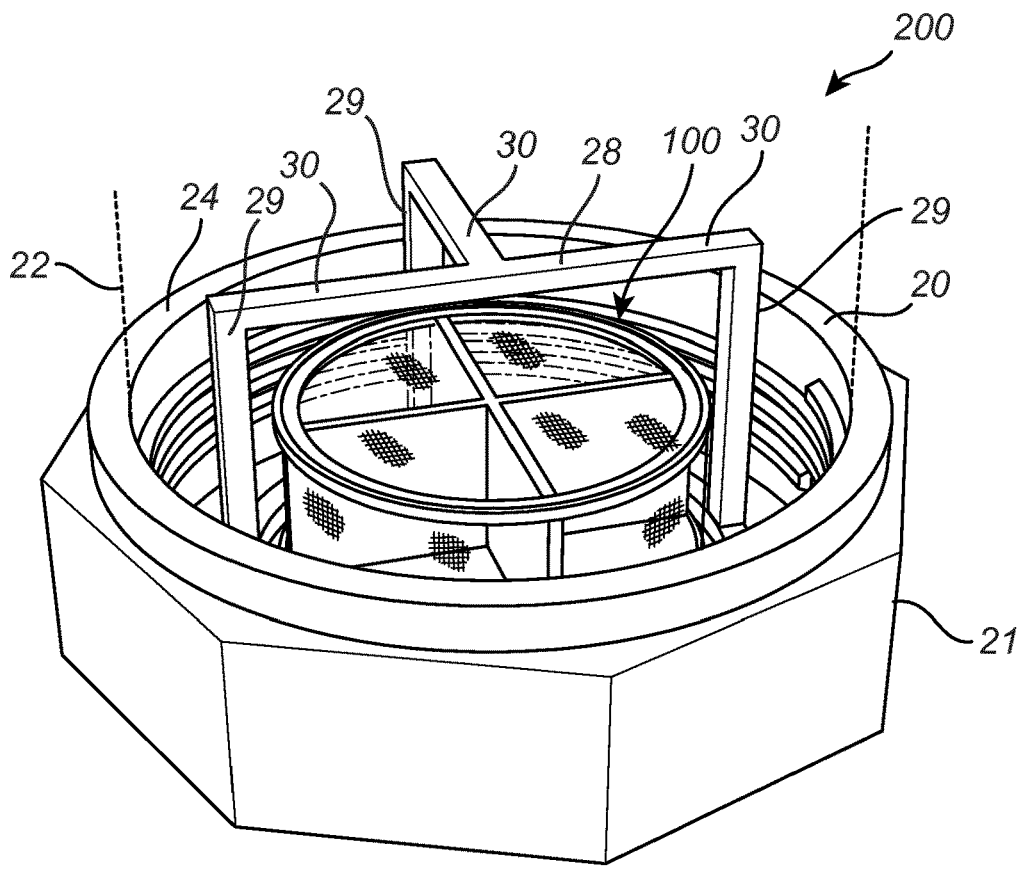

FIGS. 3A and 3B disclose a closure comprising a flow-promoting device.

Figure 4:
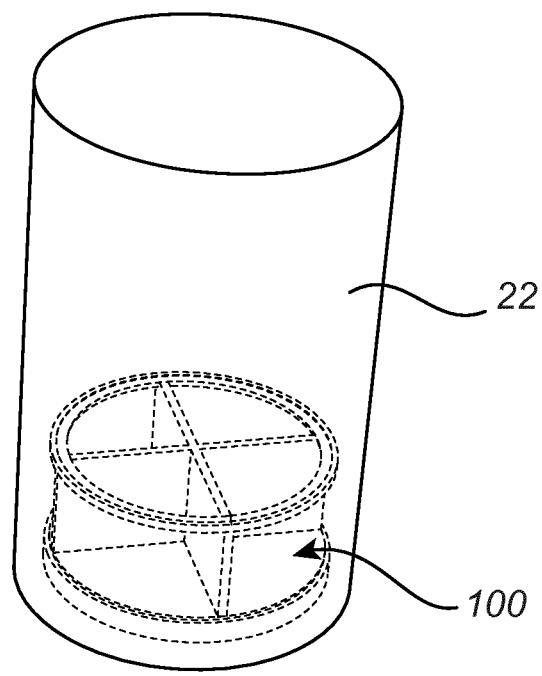

FIG. 4 discloses a flow-promoting device arranged in a vessel.

Figure 5:
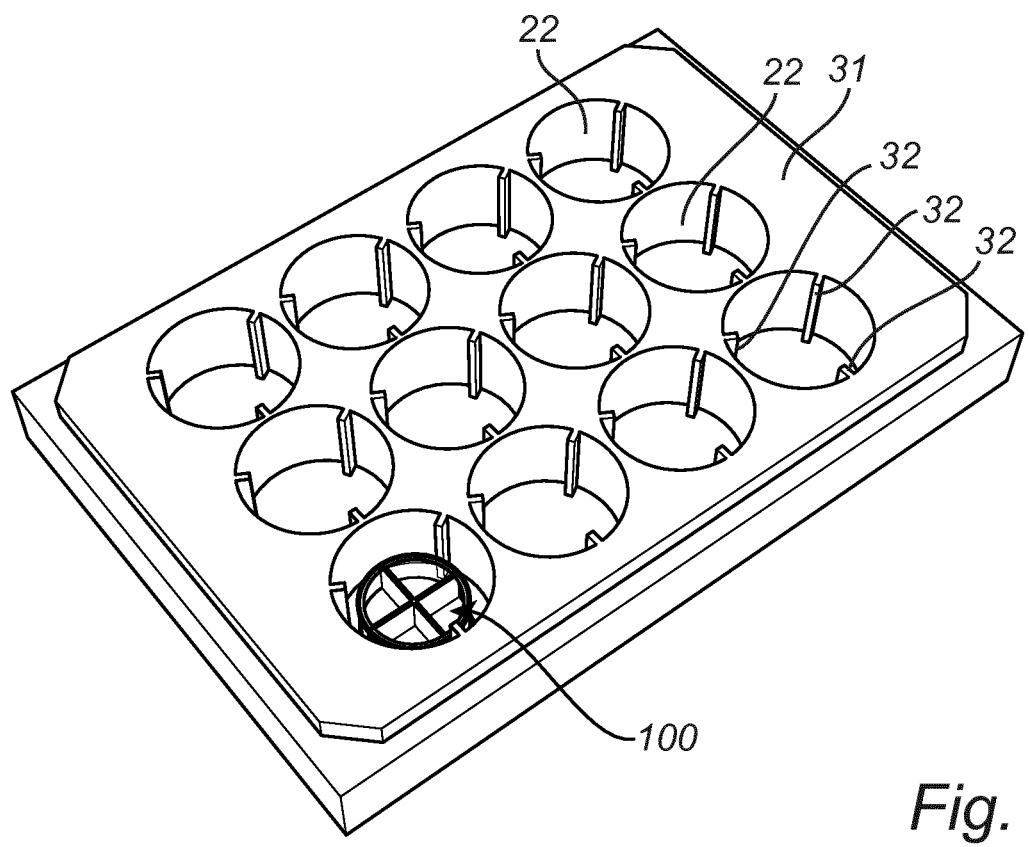

FIG. 5 discloses a tray comprising a plurality of vessels.

Figure 6:
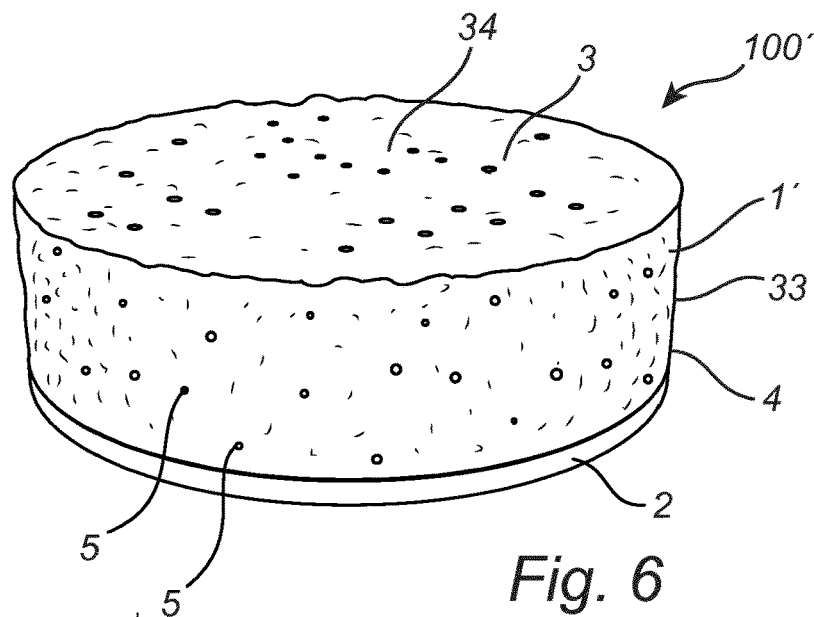

FIG. 6 discloses a second embodiment of the flow-promoting device.

Figure 7:
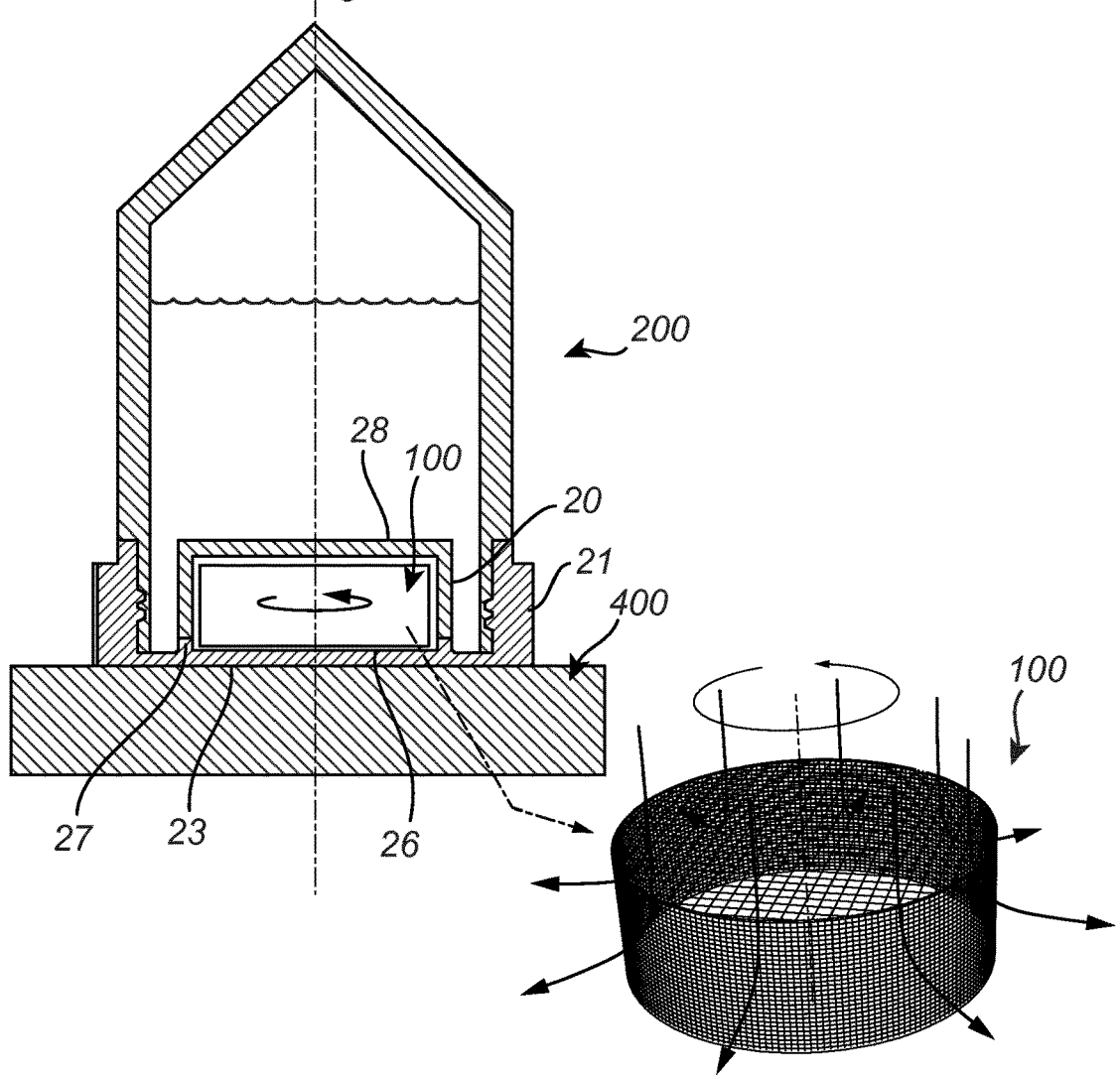

FIG. 7 discloses, highly schematically, the principle of operation of the flow-promoting device.

Figure 8:
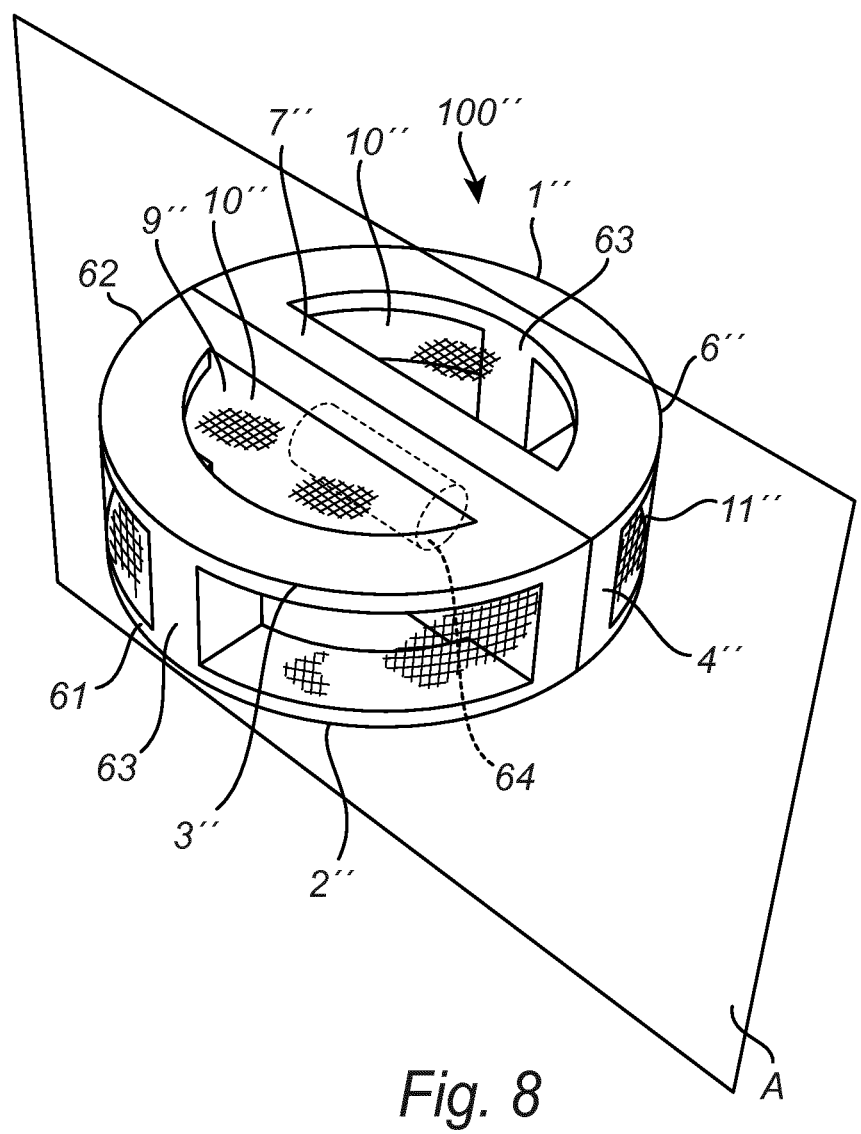

FIG. 8 discloses a third embodiment of the flow-promoting device.

DETAILED DESCRIPTION OF PREFERRED EMBODIMENTS

In the following the present invention will be discussed starting with the overall design of a first embodiment of the flow-promoting device.

FIGS. 1 and 2 disclose the flow-promoting device 100 as seen from the top and bottom respectively. The overall geometry of the flow-promoting device 100 may be seen as a puck-shape having a circular form. The diameter is larger than the height. It is however to be understood that other geometries are possible.

The flow-promoting device 100 comprises a retaining structure 1 having a bottom wall 2, a top wall 3 and a circumferential side wall 4 interconnecting the top wall 2 and the bottom wall 3. The retaining structure 1 has a compartment 9. The top wall 2 and the side wall 4 are formed by a permeable material to be described below. The retaining structure 1 may e.g. be formed by injection molding a plastic material.

The bottom wall 2 is formed as a solid disc having an essentially flat bottom surface. The bottom wall 2 comprises a ferromagnetic material 5. In the disclosed embodiment the ferromagnetic material 5 is arranged as a unitary body fixedly arranged to the bottom wall 2. It is to be understood that the ferromagnetic material 5 may be arranged in other positions and also may be arranged as particles dispersed in the plastic material during injection molding the retaining structure 1. The fixation may be made by the ferromagnetic material 5 being in-molded in the retaining structure 1, fixed thereto by using an adhesive or being received in a compartment in the retaining structure 1. Thereby the flow-promoting device 100 and the ferromagnetic material 5 will be rotated as one unit when subjected to an alternating magnetic field.

The bottom wall 2 supports a frame 6 which in the disclosed embodiment comprises four vertical and perpendicular thin partition walls 7. A ring 8 interconnects the free edges of the partition walls 7. It is to be understood that the number of partition walls 7 may differ and also that the partition walls 7 and the ring 8 may be omitted.

In the disclosed embodiment the partition walls 7 divide the compartment 9 into four chambers 10. The compartment 9 or chambers 10 are arranged to contain at least one fluid-permeable solid reaction member (not shown). The reaction member(s) may be received in the compartment 9 or chambers 10 as loose particles or received in one or several cartridges (not shown). In the case of cartridges, the cartridges should be made up by a permeable material such as a mesh material.

The frame 6 is encircled by a permeable material 11 which forms the top wall 3 and the circumferential side wall 4 of the retaining structure 11. Thereby the permeable material 11 defines the compartment 9 with the exception of the areas where the permeable material 11 abuts the partition walls 7 and the ring 8. Also, the top wall 3 has a continuous extension across its full surface extension without any central inlet opening. The permeable material 11 may be a mesh material. The mesh material should have a density that retains the fluid-permeable solid reaction members inside the compartment 9. For illustrative purpose, the mesh size is highly exaggerated.

Now turning to FIGS. 3A and 3B the flow-promoting device 100 is disclosed as forming part of a reactor arrangement 200. The flow-promoting device 100 is arranged together with a supporting structure 20 integrated in a closure 21 to be used together with a vessel 22. The vessel 22 is shown highly schematically with dotted lines.

The closure 21 comprises an exterior closed end surface 23. The exterior closed end surface 23 is preferably flat. The closed end surface 23 preferably has a surface extension that allows the vessel 22 provided with the closure 21 to be arranged in an up-right position resting on the flat end surface 23.

A circumferential wall portion 24 extends in the vertical direction from the closed end surface 23. The wall portion 24 is provided with threads 25 along its inner surface. The threads 25 allow the closure 21 to be mounted to the vessel 22.

The supporting structure 20 comprises an abutment portion 26 which is formed by an inner, horizontal surface of the closure 21. The abutment portion 26 may be provided as a flat surface. The abutment portion 26 may be provided with low friction characteristics. The low friction may be provided by the surface texture or by a low friction coating on the inner surface of the closure 21.

The supporting structure 20 further comprises a circumferential rim 27. The dimeter of the rim 27 slightly exceeds the outer diameter of the bottom wall 2 of the flow-promoting device 100. The rim 27 acts as a guide that centralizes the flow-promoting device 100 and prevents the same from wobbling when set to rotate.

The supporting structure 20 further comprises a restriction portion 28 opposite the abutment portion 26. The restriction portion 28 is in the disclosed embodiment formed by three vertical legs 29 interconnected by three horizontal struts 30. The struts 30 do not only form part of the restriction portion 28 but do also act as baffles preventing any vortex formation as the flow-promoting device 100 is set to rotate inside the supporting structure 20.

Now turning to FIG. 4 the flow-promoting device 100 is disclosed as a stand-alone unit which is submerged in a vessel 22 containing a fluidic medium. When arranging the vessel 22 on an external magnetic or electromagnetic actuator (not disclosed) and subjecting the flow-promoting device 100 to an alternating magnetic field, the flow-promoting device 100 will rotate inside the vessel 22.

FIG. 5 discloses a tray 31 comprising a plurality of vessels 22 arranged side by side in a matrix pattern. Although only one flow-promoting device 100 is illustrated, it is to be understood that one flow-promoting device 100 is arranged in each vessel 22. Thereby several reactions may run simultaneously. In the disclosed embodiment each vessel 22 comprises baffles 32 extending along the vertical side walls. The number of baffles 32 and their design may be altered. The purpose of the baffles 32 is to prevent formation of a vortex in the vessel 22 as the flow-promoting device 100 is set to rotate.

Now turning to FIG. 6, another embodiment of the flow-promoting device 100' is shown. The retaining structure 1' of the flow-promoting device 100' is formed as a body 33 comprising one or more fluid permeable self-supporting material(s) 34 of spatially homogenous or composite design. As non-limiting examples, the spatially homogenous or composite design may be provided by porous monoliths made from organic or inorganic precursors, open cell foams or sponges, porous (hydro)gels, cryogels, or a combination thereof. The fluid-permeable solid reaction members are incorporated in the one or more fluid-permeable self-supporting material(s) 34. The outer boundaries provided by such permeable self-supporting material(s) will form the top wall 3 and the circumferential side wall 4 of the retaining structure 1'. The body 33 is disclosed as arranged to a supporting bottom wall 2. This bottom wall 2 may be omitted.

The body 33 forming the retaining structure 1' comprises particulate ferromagnetic material 5. The ferromagnetic material is integrated and distributed in the body 33. The integration and distribution may be homogenous or restricted to well-defined areas such as across a layer integrated in the body 33. Also the ferromagnetic material 5 may be arranged as a unitary body, such as a bar magnet.

The retaining structure 1' may by way of example have a puck-shape, however it is to be understood that other geometries are possible.

In the following, with reference to FIG. 7, the use of a reactor arrangement 200 comprising a closure 21, a supporting structure 20 and a flow-promoting device 100 of the type described above will be discussed. The reactor arrangement 200 is disclosed as standing on a magnetic or electromagnetic actuator 400.

To prepare the process, the flow-promoting device 100 is arranged to be removably received in a supporting structure 20 of the closure 21. The flow-promoting device 100 is arranged between the restriction portion 28 and the abutment portion 26. The flow-promoting device 100 will thereby be retained inside the supporting structure 20 as seen in a direction perpendicular to the abutment portion 26. Thereby the flow-promoting device 100 is prevented from falling out of the supporting structure 20 during handling of the closure 21.

The vessel 22 is filled with a fluidic medium and then sealed with the closure 21. The vessel 22 is turned up-side down and arranged standing on the magnetic or electromagnetic actuator 400 resting on the flat exterior end surface 23 of the closure 21.

When activating the magnetic or electromagnetic actuator 400, an alternating magnetic field is generated which will cause the flow-promoting device 100 to rotate inside the supporting structure 20. During the rotation, the flow-promoting device 100 will be guided and prevented from wobbling by the rim 27 of the supporting structure 20.

As a result of the rotation, the fluidic medium will be caused to aspirate via at least the top wall 3 which is mainly made of a permeable material 11, into the compartment 9 of the retaining structure 1 and hence come in contact with the at least one fluid-permeable solid reaction members arranged in the compartment 9 before being discharged via the fluid permeable circumferential side wall 4. The at least one fluid-permeable solid reaction members will accordingly be percolated by said fluidic medium, allowing at least one agent distributed in the fluidic medium to undergo a chemical process such as a biological or chemical transformation, or a physical or chemical trapping from, or release of agents to the fluidic medium.

Since the top wall 3 is mainly made of a permeable material 11, the fluidic medium will be allowed to be aspirated across essentially the full surface area of the top wall 3, whereby no vortex is formed that may cause entrapment of gas or form gas locking in/around the fluid-permeable solid reaction members.

Further, by the walls of the retaining structure 1 being formed mainly by a permeable material 11 and whereby the fluidic medium is allowed to aspirate into the compartment 9 of the retaining structure 1 across the full area of the top wall, the available contact surface between the fluidic medium and the fluid-permeable solid reaction members may be substantially increased as compared to prior art devices which use a central inlet and radially extending outlet channels.

During the rotation of the flow-promoting device 100, the struts 30 will prevent any vortex formation.

When the reaction is deemed to be finished, the vessel 22 is removed from the magnetic or electromagnetic actuator 400 and the closure 21 is removed.

Depending on the type of reaction, the closure 21 together with the flow-promoting device 100 may be removed from the vessel 22 and the fluid and then be transferred to another vessel with another fluid where the process may be repeated anew. A typical situation is where the solid reaction members contained in the flow-promoting device 100 are used to trap a chemical substance in the first fluid, and where the trapped substance is to be eluded in a second fluidic medium. Alternatively, the used closure 21 together with its used flow-promoting device 100 may be discharged while the fluidic medium in the vessel 22 is further treated. As a yet another alternative the used flow-promoting device 100 may be replaced by a new flow-promoting device 100 with another type of solid reaction members.

Now turning to FIG. 8, yet another embodiment of the flow-promoting device 100" is shown. The flow-promoting device 100" has a puck-shape having a circular form with a diameter being larger than the height. It is however to be understood that other geometries are possible.

The flow-promoting device 100" comprises a retaining structure 1" comprising a bottom wall 2", a top wall" 3" and a circumferential side wall 4". The bottom wall 2", the top wall 3" and the circumferential side wall 4" are mainly formed by a permeable material 11". The permeable material 11" is expanded by a frame 6" which comprises a lower ring 61 and an upper ring 62 interconnected by two legs 63 and a partition wall 7". The two legs 63 are arranged on opposite sides of a geometrical plane A that extends through the center of the flow promoting device 100" and in parallel with a rotational axis of the flow-promoting device 100". The partition wall 7" coincides with said geometrical plane A and divides the compartment 9" defined by the frame 6" and the permeable material 11" into two chambers 10", one chamber on each side of the partition wall 7".

The partition wall 7" comprises a fixedly arranged longitudinal body 64 of a ferromagnetic material, such as a bar magnet. The ferromagnetic body 64 has a longitudinal extension coinciding with the geometrical plane A. The fixation of the ferromagnetic body 64 may be made e.g. by in-molding the same in the partition wall 7".

The chambers 10" are arranged to contain at least one fluid-permeable solid reaction member (not shown). The reaction member(s) may be received in the compartment 9" or the chambers 10" as loose particles or be received in one or several cartridges (not shown). In the case of cartridges, the cartridges should be made up by a permeable material such as a mesh material.

As given above, the frame 6" is encircled by a permeable material 11" which forms the bottom wall 2", the top wall 3" and the circumferential side wall 4". Thereby the permeable material 11" defines the compartment 9" with the exception of the areas where the permeable material 11" abuts the frame 6". The permeable material 11" can by way of example be arranged on the outside, as disclosed) or on the inside of the retaining structure 1".

The bottom wall 2" and the top wall 3" do each have a continuous extension across its full surface extension without any central inlet opening.

The bottom wall 2" and the top wall 3" are essentially identical whereby the flow-promoting device 100" may be turned up-side-down with remained function.

As an effect of the bottom wall 2" and the top wall 3" both mainly being made of a permeable material 11", the fluidic medium is, during operation, allowed to aspirate into the compartment 9" across the full area of not only the top wall 3" but also the bottom wall 2" before leaving via the circumferential side wall 4". More precisely, when the flow-promoting device 100" is set to rotate in a vessel 22, the device 100" will rotate with its bottom wall 3" facing and abutting the bottom of the vessel 22 or the abutment surface 26 of a supporting structure 20. However, a slight lifting action will occur, whereby the fluidic medium also is allowed to enter the device 100" via the bottom wall 2" before leaving the device 100" via the circumferential side wall 4".

The person skilled in the art realizes that the present invention by no means is limited to the preferred embodiments described above. On the contrary, many modifications and variations are possible within the scope of the appended claims.

The compartment has been described a volume expanded by a frame and defined by a permeable material. It is to be understood that the compartment, with remained function, may be defined by the permeable material having an inherent stiffness forming a self-supporting retaining structure. The self-supporting retaining structure may be formed e.g. by pressing a mesh material. In case of the permeable material having an inherent stiffness, the permeable material may be formed as a container into which the solid reaction members or cassettes containing solid reaction member are arranged before interconnecting the bottom wall and the permeable material.

The frame has been described as being encircled by a permeable material which forms a top wall and a circumferential side wall. In case the fluid-permeable solid reaction members are arranged to be contained in cartridges, the walls of such cartridges may be made of a permeable material, whereby one or several such cartridges may be arranged e.g. side by side, to thereby together form a top wall and a circumferential side wall mainly formed by a permeable material.

The closure and the supporting structure are disclosed as one integral unit. It is however to be understood that the supporting structure may be provided as a stand-alone unit.

Additionally, variations to the disclosed embodiments can be understood and effected by the skilled person in practicing the claimed invention, from a study of the figures, the disclosure, and the appended claims. In the claims, the word "comprising" does not exclude other elements or steps, and the indefinite article "a" or "an" does not exclude a plurality.

The invention claimed is:

1. A rotatable flow-promoting device for performing a biological or chemical transformation, or physical or chemical trapping from, or release of agents to, a fluidic medium, wherein
   said flow-promoting device comprising a ferromagnetic material and a retaining structure, the retaining structure having a compartment defined by a permeable mesh material, wherein
   the retaining structure comprises a top wall and a circumferential side wall, wherein the top wall and the circumferential side wall are formed mainly by said permeable mesh material, and
   the compartment of the retaining structure is configured to contain at least one fluid-permeable solid reaction member, whereby
   when the flow-promoting device is submerged into a fluidic medium and the flow-promoting device is subjected to an alternating magnetic field, the flow-promoting device is set to rotate, thereby causing a flow of fluidic medium into and through the compartment via said permeable mesh material,
   wherein the top wall has a continuous extension across its full surface extension and does not comprise any central inlet opening.

2. The flow-promoting device according to claim 1, wherein said permeable mesh material has an inherent stiffness thereby forming a self-supporting retaining structure, or said mesh material being supported by a frame that expands said compartment.

3. The flow-promoting device according to claim 2, wherein the retaining structure comprises at least one partition wall dividing the compartment into at least two chambers.

4. The flow-promoting device according to claim 2, wherein the compartment is arranged to receive at least one cartridge adapted to contain the at least one fluid-permeable solid reaction member.

5. The flow-promoting device according to claim 1, wherein the ferromagnetic material is a unitary body fixedly arranged to the retaining structure.

6. The flow-promoting device according to claim 1, wherein the ferromagnetic material is a longitudinal body fixedly arranged to the flow-promoting device and extending in a geometrical plane extending through a centre of the flow-promoting device, wherein the geometrical plane coincides with a rotational axis of the flow-promoting device.

7. A method of using a flow-promoting device for performing a biological or chemical transformation, or physical or chemical trapping from, or release of agents to, a fluidic medium, said method comprising:
   providing the flow-promoting device according to claim 1;
   submerging the flow-promoting device into a fluidic medium; and
   subjecting the flow-promoting device to an alternating magnetic field to cause the flow-promoting device to rotate, thereby causing a flow of fluidic medium into and through the compartment via said permeable mesh material.

8. A flow-promoting device for performing a biological or chemical transformation, or physical or chemical trapping from, or release of agents to, a fluidic medium, wherein:
   said flow-promoting device comprising a ferromagnetic material and a body formed by a fluid-permeable material, wherein the body comprises a top wall and a circumferential side wall, wherein the top wall and the circumferential side wall are formed mainly by said fluid-permeable material, and the fluid-permeable material contains at least one fluid-permeable solid reaction member, whereby when the flow-promoting device is submerged into a fluidic medium and the flow-promoting device is subjected to an alternating magnetic field, the flow-promoting device is set to rotate, thereby causing a flow of fluidic medium into and through said fluid-permeable material, wherein the fluid-permeable material includes one or more fluid-permeable self-supporting material(s) of spatially homogenous or composite design, which are provided by porous monoliths made from organic or inorganic precursors, open cell foams or sponges, porous (hydro)gels, cryogels, or a combination thereof, and wherein the ferromagnetic material is particulate, and is integrated and distributed in the body.

9. A reactor arrangement, the reactor arrangement comprising a rotatable flow-promoting device and a supporting structure, the rotatable flow promoting device comprising a ferromagnetic material and a retaining structure, the retaining structure having a compartment defined by a permeable mesh material, wherein the retaining structure comprises a top wall and a circumferential side wall, wherein the top wall and the circumferential side wall are formed mainly by said permeable mesh material, and the compartment of the retaining structure is arranged to contain at least one fluid-permeable solid reaction member, wherein the top wall has a continuous extension across its full surface extension and does not comprise any central inlet opening, whereby when the rotatable flow-promoting device is submerged into a fluidic medium and the rotatable flow-promoting device is subjected to an alternating magnetic field, the rotatable flow-promoting device is set to rotate, thereby causing a flow of fluidic medium into and through the compartment via said permeable mesh material; and wherein the supporting structure is arranged to removably receive the rotatable flow-promoting device, and allow the rotatable flow-promoting device to rotate inside the supporting structure when subjected to the alternating magnetic field.

10. The reactor arrangement according to claim 9, wherein the supporting structure comprises an abutment portion against which the rotatable flow-promoting device is arranged to abut during rotation.

11. The reactor arrangement according to claim 10, wherein the supporting structure further comprises a restriction portion opposite the abutment portion, wherein the rotatable flow-promoting device is arranged to be removably received between said restriction portion and said abutment portion.

12. The reactor arrangement according to claim 11, further comprising a closure arranged to be mounted to a vessel, and wherein the supporting structure is removably arranged to the closure, fixed to the closure or integrally formed with the closure.

* * * * *